(12) United States Patent
Jaworski

(10) Patent No.: US 8,582,104 B2
(45) Date of Patent: Nov. 12, 2013

(54) OPTICAL DEVICE FOR DETECTION OF AN AGENT

(75) Inventor: Frank B. Jaworski, Goleta, CA (US)

(73) Assignee: Raytheon Company, Waltham, MA (US)

( * ) Notice: Subject to any disclaimer, the term of this patent is extended or adjusted under 35 U.S.C. 154(b) by 197 days.

(21) Appl. No.: 13/173,221

(22) Filed: Jun. 30, 2011

(65) Prior Publication Data
US 2013/0003067 A1   Jan. 3, 2013

(51) Int. Cl.
*G01N 21/00* (2006.01)
*G01N 21/59* (2006.01)
*G02B 6/00* (2006.01)
*G02B 6/42* (2006.01)
*G01J 1/04* (2006.01)

(52) U.S. Cl.
USPC ............... 356/433; 356/432; 385/15; 385/30; 422/82.11; 422/82.06

(58) Field of Classification Search
USPC .................. 356/432–444, 246, 417, 480, 483; 385/15, 30, 123; 359/337.2; 250/492.1, 250/458.1; 422/82.11, 82.06, 82.07, 82.08, 422/82.09
See application file for complete search history.

(56) References Cited

U.S. PATENT DOCUMENTS

| | | | |
|---|---|---|---|
| 7,027,467 B2 * | 4/2006 | Baev et al. | 372/6 |
| 7,389,025 B2 | 6/2008 | Smith et al. | |
| 7,391,517 B2 * | 6/2008 | Trebbia et al. | 356/432 |
| 7,432,753 B2 * | 10/2008 | Onodera | 327/269 |
| 7,595,890 B2 * | 9/2009 | Fan et al. | 356/480 |
| 7,667,200 B1 * | 2/2010 | Watts et al. | 250/338.1 |
| 2002/0097401 A1 * | 7/2002 | Maleki et al. | 356/436 |
| 2005/0035278 A1 | 2/2005 | Margalit et al. | |
| 2005/0110992 A1 | 5/2005 | Scherer et al. | |
| 2005/0207943 A1 | 9/2005 | Puzey | |
| 2006/0062508 A1 * | 3/2006 | Guo et al. | 385/12 |
| 2006/0072875 A1 * | 4/2006 | Bhagavatula et al. | 385/30 |
| 2006/0227331 A1 * | 10/2006 | Vollmer et al. | 356/483 |
| 2007/0211985 A1 | 9/2007 | Duer | |
| 2008/0204758 A1 * | 8/2008 | Yates et al. | 356/480 |
| 2008/0265147 A1 | 10/2008 | Fan et al. | |
| 2009/0237666 A1 | 9/2009 | Vollmer et al. | |
| 2009/0310140 A1 * | 12/2009 | Smith et al. | 356/480 |
| 2010/0243448 A1 * | 9/2010 | Maurer et al. | 204/450 |

(Continued)

OTHER PUBLICATIONS

Hu et al., "Si-CMOS-compatible lift-off fabrication of low-loss planar chalcogenide waveguides," *Optics Express*, vol. 15, No. 19, Sep. 17, 2007.

Hu et al., "Demonstration of chalcogenide glass racetrack microresonators," *Optics Letters*, vol. 33, No. 8, pp. 761-763, Apr. 15, 2008.

Jaworski et al, U.S. Appl. No. 12/503,264 "Optical Device for Detection of Agent" patent application filed Jul. 15, 2009.

(Continued)

*Primary Examiner* — Sang Nguyen
(74) *Attorney, Agent, or Firm* — Lando & Anastasi, LLP (57) ABSTRACT

In certain embodiments, a system for detecting an agent includes a resonator device configured to receive an agent. The resonator device is additionally configured to transmit light received from a light source. The transmitted light has a known characteristic in the absence of the received agent and an altered characteristic in the presence of the received agent. The system further include a lens positioned between the resonator device and a detector array. The lens is configured to focus the transmitted light onto one or more detectors of the detector array, the one or more detectors of the detector array operable to generate a signal corresponding to the transmitted light. The system further includes a processing system operable to determine whether the agent is present based on the signal generated by the one or more detectors of the detector array.

24 Claims, 4 Drawing Sheets

(56) References Cited

U.S. PATENT DOCUMENTS

| | | | |
|---|---|---|---|
| 2011/0080579 A1* | 4/2011 | Pipino | 356/301 |
| 2011/0256577 A1* | 10/2011 | Himmelhaus et al. | 435/29 |
| 2011/0295511 A1* | 12/2011 | Sanders et al. | 702/19 |
| 2012/0154810 A1* | 6/2012 | Jaworski et al. | 356/432 |

OTHER PUBLICATIONS

Jaworski et al, U.S. Appl. No. 12/948,453 "Optical Device for Detection of Agent" patent application filed Nov. 27, 2010.

Jaworski et al, U.S. Appl. No. 12/948,485 "Optical Device for Detection of Agent" patent application filed Nov. 17, 2010.

* cited by examiner

OPTICAL DEVICE FOR DETECTION OF AN AGENT

BACKGROUND

Detector arrays, such as focal plane arrays (FPAs), generally comprise a number of photo-detectors each operable to generate a signal corresponding to one or more characteristics of light incident on the surface of the detector array. Imaging devices commonly use detector arrays to generate digital images. In such applications, the photo-detectors of the detector array each generate a signal corresponding to light generated and/or reflected by an object. The generated signals may be collected and combined such that a digital image of the object that generated and/or reflected the light may be generated.

SUMMARY

According to embodiments of the present disclosure, disadvantages and problems associated with previous systems for detection of an agent may be reduced or eliminated.

In certain embodiments, a system for detecting an agent includes a resonator device configured to receive an agent. The resonator device is additionally configured to transmit light received from a light source. The transmitted light has a known characteristic in the absence of the received agent and an altered characteristic in the presence of the received agent. The system further include a lens positioned between the resonator device and a detector array. The lens is configured to focus the transmitted light onto one or more detectors of the detector array, the one or more detectors of the detector array operable to generate a signal corresponding to the transmitted light. The system further includes a processing system operable to determine whether the agent is present based on the signal generated by the one or more detectors of the detector array.

Particular embodiments of the present disclosure may provide one or more technical advantages. For example, because the system of present disclosure may provide for the detection of an agent using a detector array (e.g., an FPA) that may be common in certain imaging devices, one or more components of the system of the present disclosure may be integrated with or form part of an imaging device, thereby reducing the size, weight, cost, and/or power requirements the system of the present disclosure, as compared to certain conventional systems. Additionally, because the light transmitted by the one or more resonators of the resonator device passes through one or more lenses configured to focus the light onto the one or more detectors of a detector array, the resonator device may be located separate from the detector array. In embodiments in which detector array is maintained at a low operating temperature (e.g., embodiments in which detector array is an FPA having a cryogenic operating temperature), the resonator device being located separate from detector array may eliminate the need to maintain the resonator device at the low operating temperature of the detector array. Additionally, the resonator device being located separate from the detector array may allow the resonator device to be positioned such that an gent is more easily and/or more likely to be received. As just one example, in embodiments in which the system of the present disclosure is incorporated into a portable device, such as a digital camera having an FPA, the one or more lenses may allow the resonator device to be located separate from the FPA, such as on the existing lens housing of the digital camera. As a result, an agent may be more readily absorbed, such as from the air to which the digital camera is exposed (as opposed to the agent being deposited on the resonator device, as may be necessary if resonator device were not located separate from the FPA).

Certain embodiments of the present disclosure may include some, all, or none of the above advantages. One or more other technical advantages may be readily apparent to those skilled in the art from the figures, descriptions, and claims included herein.

BRIEF DESCRIPTION OF THE DRAWINGS

To provide a more complete understanding of the present disclosure and the features and advantages thereof, reference is made to the following description taken in conjunction with the accompanying drawings, in which.

DESCRIPTION OF EXAMPLE EMBODIMENTS

Figure 1:
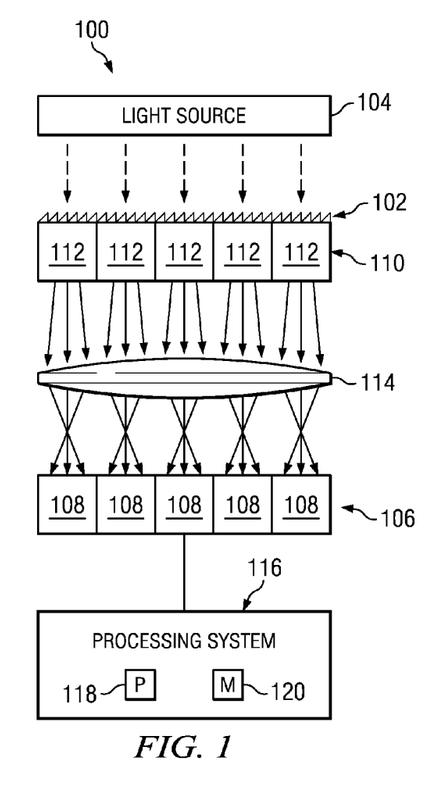
FIG. 1 illustrates an example system for detecting an agent, according to certain embodiments of the present disclosure.

FIG. 1 illustrates an example system 100 for detecting an agent 102, according to certain embodiments of the present disclosure. System 100 may include one or more light sources 104, a detector array 106 comprising one or more detectors 108, and resonator device 110 comprising one or more resonators 112. One or more of resonators 112 may be configured to receive (e.g., absorb) an agent 102. System 100 may additionally include one or more lenses 114 positioned between resonator device 110 and detector array 106, the one or more lenses 114 being configured to focus light passing through resonators 112 onto one or more detectors 108 of detector array 106. In certain embodiments, the one or more detectors 108 of detector array 106 are configured to communicate with a processing system 116 operable to identify an agent 102 (or identify a family of agents to which agent 102 belongs) based on one or more characteristics of light sensed by detectors 108 of detector array 106. Although this particular implementation of system 100 is illustrated and primarily described, the present disclosure contemplates any suitable implementation of system 100, according to particular needs.

In general, system 100 is operable to detect the presence of an agent 102. Agent 102 may refer to one or more atoms or molecules of any chemical, biological, and/or physical matter the presence of which may be detected by system 100. As just example, agent 102 may include a hazardous substance such as a chemical or biological agent. Furthermore, one or more components of system 100 may be in incorporated into a handheld device to be carried by military personnel, the handheld device operable to detect chemical or biological agent 102 (e.g., in the air, in water, or in any other suitable medium) such that the military personnel may be alerted to the presence of the chemical or biological agent 102. Although a particular application of system 100 (e.g., an application in which one or more components incorporated into a handheld device to be carried by military personnel) is described above, the present disclosure contemplates any suitable application of system 100, according to particular needs.

System 100 may detect an agent 102 based on signal generated by detectors 108 of detector array 106. More particularly, detectors 108 of detector array 106 may be operable to generate signals corresponding to one or more characteristics of light (e.g., intensity and/or peak wavelength) transmitted by a resonators 112 of resonator device 110. Because a resonator 112 may have known optical properties, light transmitted by the resonator 112 may have known characteristics. Thus, the signal generated by detectors 108 of detector array 106 may also be known (i.e., a signal generated by transmitted light received by detectors 108 having known characteristics corresponding to the known optical properties of the resonator 110).

If agent 102 is received by (e.g., absorbed on a surface of) one or more resonators 112 of resonator device 110, the characteristics of the light transmitted by the one or more resonators 112 may be altered by the agent 102. For example, agent 102 may absorb an amount of the transmitted light (i.e., decrease the intensity of the transmitted light). Additionally or alternatively, agent 102 may alter a peak wavelength of the transmitted light. As a result of the change in the characteristics of the light transmitted by the one or more resonators 112, the signal generated by detectors 108 of detector array 106 may differ from the known signal (i.e., an altered signal may be generated). Thus, when the signal generated by a particular detector 108 of detector array 106 differs from the known signal associated with that detector 108, it may be determined that an agent 102 is present on the surface of the resonator 110 corresponding to the detector 108.

Because system 100 may provide for the detection of an agent using a detector array 106 (e.g., an FPA) that may be common in certain imaging devices, one or more components of system 100 may be integrated with or form part of an imaging device, thereby reducing the size, weight, cost, and/or power requirements of system 100, as compared to certain conventional systems. Additionally, because the light transmitted by the one or more resonators 112 of resonator device 110 passes through one or more lenses 114 configured to focus the light onto the one or more detectors 108 of detector array 106, resonator device 110 may be located separate from detector array 106. In embodiments in which detector array 106 is maintained at a low operating temperature (e.g., embodiments in which detector array 106 is an FPA having a cryogenic operating temperature), resonator device 110 being located separate from detector array 106 may eliminate the need to maintain resonator device 110 at the low operating temperature of the detector array 106. Additionally, resonator device 110 being located separate from detector array 106 may allow resonator device 106 to be positioned such that an gent 102 is more easily and/or more likely to be received. As just one example, in embodiments in which system 100 is incorporated into a portable device, such as a digital camera having an FPA, the one or more lenses 114 may allow resonator device 110 to be located separate from the FPA, such as on the existing lens housing of the digital camera. As a result, an agent 102 may be more readily absorbed, such as from the air to which the digital camera is exposed (as opposed to the agent 102 being deposited on the resonator device 110, as may be necessary if resonator device were not located separate from the FPA).

Light sources 104 may include any suitable devices operable to emit an amount of light such that the emitted light may be received by one or more resonators 110. For example, light sources 104 may include a quantum dot light emitting diode (LED), a laser, or any other suitable light source, according to particular needs. Additionally, one or more light sources 104 may include broadband light sources operable to emit an amount of light having a range of peak wavelengths.

Figure 4:
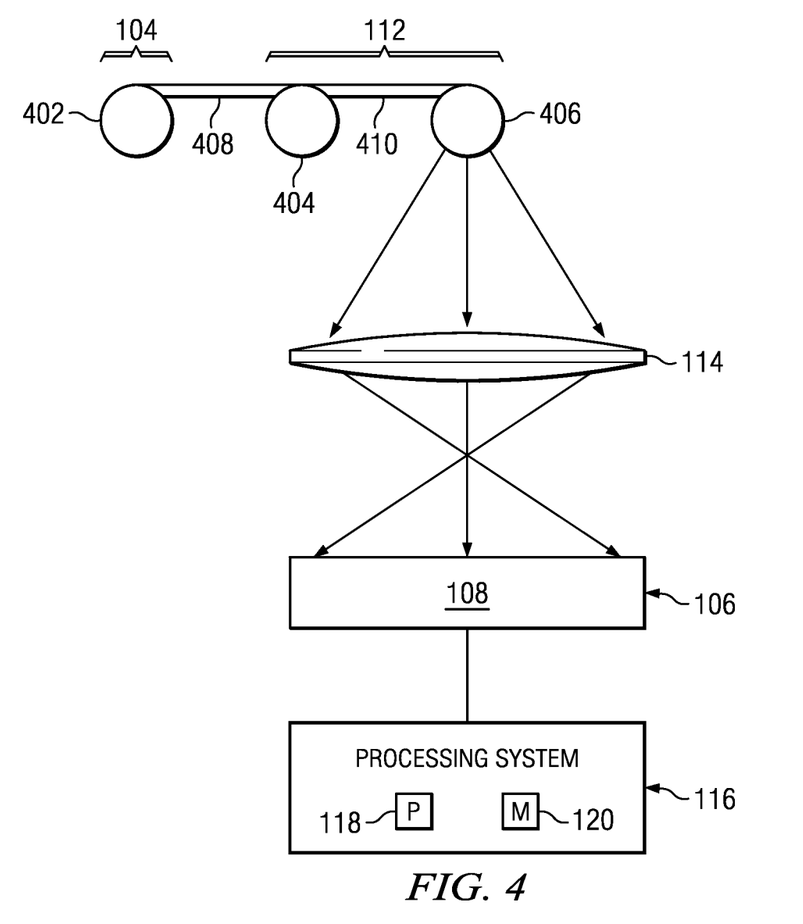
FIG. 4 illustrates an example alternative system for detecting an agent, according to certain embodiments of the present disclosure.

In certain embodiments, a single light source 104 may provide light received by each resonator 112 of resonator device 110. In certain other embodiments, a separate light source 104 may provide light received by each resonator 112 of resonator device 110. For example, as depicted in FIG. 4 and discussed in detail below, light sources 104 may include a plurality of emitter optical resonators 402. Each emitter optical resonator 402 may be coupled to a resonator 112 of resonator device 110 (e.g., including a functionalized resonator 404 and a reference optical resonator 406) via a waveguide (e.g., waveguides 408 and 410).

Detector array 106 may be a focal plane array (FPA), active pixel sensor (APS), or any other suitable light sensing device operable to generate a signal corresponding to one or more characteristics of light incident upon detector array 106. Detector array 106 may include any suitable number of detectors 108, and each detector 108 may be operable to generate a signal (e.g., accumulate charge or produce a current and/or voltage) in response to light incident upon the detector 108. For example, detectors 108 may include a position sensitive detector (PSD), photodiode, and/or any other suitable device for accumulating a charge and/or producing a current and/or voltage in response to light incident upon the detector 108.

In certain embodiments, detector array 106 may be a component of a digital camera, video camera, or any other photographic and/or image capturing device. In such applications, the signal generated by detectors 108 (e.g., the charge accumulated or the current and/or voltage produced) may be further processed (e.g., by processing system 112, described below) to create an image representative of an object emitting and/or reflecting the incident light. In other words, the signal generated by each detector 108 may correspond to a pixel in a captured electronic image.

The one or more resonators 112 of resonator device 110 may each include any suitable device constructed from any suitable material that has known optical properties. In other words, each resonator 112 may be any suitable device that is configured to receive light from light source 104 and transmit the received light such that the transmitted light has known characteristics (e.g., intensity and/or peak wavelength). For example, resonators 112 may be devices constructed of chalcogenide glass and configured to receive broadband light from light source 104 and transmit light having a particular peak wavelength (or range of peak wavelengths). In other words, resonators 112 may filter the broadband light received from light source 104 such that light having a particular wavelength (or range of peak wavelengths) is transmitted from resonators 112.

In certain embodiments, resonators 112 comprise waveguides configured in a closed loop known as an optical ring such that light received from lights source 104 of the appropriate wavelengths are coupled to the loop, the light increasing in intensity over multiple round-trips due to constructive interference. Other wavelengths of light received from light source 104 may decrease in intensity due to destructive interference. In certain other embodiments, resonators 112 comprise an arrangement of mirrors known as an optical cavity, the optical cavity being configured to form a standing wave for one or more wavelengths.

The one or more lenses 114 positioned between resonator device 110 and detector array 106 may each comprise any suitable material having any suitable configuration such that light transmitted by resonators 112 of resonator device 110 is focused onto one or more corresponding detectors 108 of detector array 106. For example, each lens 114, in order to focus light transmitted by a corresponding resonator 112 onto a corresponding detector 108, may dimensioned based on the distance positioned from the corresponding resonator device 110, the distance positioned from the corresponding detector 108 of detector array 106, the size of the corresponding detector 106, and/or any other suitable property of system 100.

Although a single lens 114 is depicted as focusing light transmitted by each resonator 112 onto a single corresponding detector 108 of detector array 106, the present disclosure contemplates any suitable number of lenses 114 focusing light transmitted by each resonator 112 onto any suitable number of corresponding detector 108 of detector array 106, according to particular needs. For purposes of simplicity, a single lens 114 will be described as focusing light transmitted by each resonator 112 onto a single corresponding detector 108 throughout the remainder of this description.

Resonators 112 of resonator device 110 may each be configured to receive agent 102, and agent 102 may alter the known characteristics of light transmitted by the resonators 110 (as described in further detail below). Resonators 112 may receive agent 102 in any suitable manner. For example, resonators 112 may be configured to receive an agent 102 by absorbing the agent 102 from a liquid including the agent 102, which may be deposited on a surface of resonators 110 (e.g., by a user of system 100). Alternatively, resonators 112 may be configured to receive an agent 102 (e.g., an airborne agent) by absorbing the agent from air containing the agent 102. Furthermore, one or more resonators 110 may be functionalized (e.g., by coating a surface with artificial antibodies using a polymer technique) such that the one or more resonators 112 attract only certain agents 102 or families of agents 102.

If an agent 102 is received (e.g., absorbed) by one or more resonators 112, the agent 102 may alter the characteristics of light transmitted by the one or more resonators 112. For example, certain agents 102 may absorb a particular amount of received light (i.e., decrease the intensity of light as compared to a known intensity based on the optical properties of the resonator 112), other agents 102 may change the index of refraction of the resonators 112 (thereby changing the peak wavelength of light transmitted by the resonators 112 relative to a known peak wavelengths based on the optical properties of the resonators 112), and still other agents 102 may both absorb a particular amount of light and change the index of the resonators 112. As one particular example, an agent 102 consisting of carbon tetrachloride, when deposited on a resonator 112, may change the index of refraction of the resonator 112, thereby changing the peak wavelength of light transmitted by the resonator 112 relative to a known peak wavelength based on the optical properties of the resonator 112.

As described above, resonators 112 have known optical properties. Due to these known optical properties, resonators 112 transmit light having known characteristics such that the signals to be generated by the detectors 108 corresponding to the resonators 112 (in the absence of an agent 102) may be known. Because an agent 102 may alter one or more characteristics of light transmitted by resonators 112, in the presence of an agent 102, the signals generated by the corresponding detectors 108 may differ from the known signal (i.e., detectors 108 may generate altered signals rather than known signals). Thus, by determining whether a signal generated by a detector 108 differs from the known signal associated with the detector 108, whether an agent 102 is present may also be determined (as described in further detail below). Additionally, because different agents 102 may alter one or more characteristics of light transmitted by resonators 112 in different ways (which may affect the degree of difference between the altered signal and the known signal), the way in which the characteristics of light transmitted by resonators 110 is altered may be used to identify agent 102 or the family of agent 102 (as described in further detail below).

Processing system 116 of system 100 may include any suitable combination of software, firmware, and hardware may comprise a personal computer, workstation, network computer, kiosk, wireless data port, personal data assistant (PDA), one or more processors within these or other devices, or any other suitable processing device. Processing system 116 may include one or more processing modules 118, which may include one or more microprocessors, controllers, or other suitable computing devices or resources that may work either alone or with other components of system 100 to provide a portion or all of the functionality of system 100 described herein. Processing system 116 may also include one or more memory modules 120, which may take the form of volatile or non-volatile memory including, without limitation, magnetic media, optical media, random access memory (RAM), read-only memory (ROM), removable media, or any other suitable memory component.

Additionally or alternatively, processing system 116 may comprise a read-out integrated circuit (ROIC) hybridized to detector array 106, the ROIC having any suitable processing components and memory components (e.g., processing module 118 and memory module 120), according to particular needs. Although processing system 116 is primarily described as being either of the above described systems, the present disclosure contemplates processing system 112 being any suitable system operable to perform the functionality described below.

Processing system 116 may be operable to access signals generated by the one or more detectors 108 of detector array 106, and to determine if an agent 102 is present (i.e., absorbed on the surface of one or more resonators 112). In response to an input (e.g., a user request), at any suitable time interval without user input (e.g., periodically determining if an agent has been received, for example, absorbed from air), or in response to any other suitable input, processing system 116 may access signals generated by one or more detectors 108 of detector array 106 and determine if an agent 102 is present. Additionally, if processing system 116 determines that an agent 102 is present, processing system 112 may be further operable to identify the agent 102 (or a family of the agent 102).

In certain embodiments, processing system 116 determines if an agent 102 is present by analyzing the accessed signals to determine if one or more of the signals indicate a change in intensity of light received by the detectors 108 generating the one or more signals. For example, processing system 116 may access the signal generated by a particular detector 108 and compare the generated signal with a known signal associated with the particular detector 108. The known signal associated with the particular detector 108 may be stored in memory module 120 or at any other suitable location in system 100 such that the known signal may be accessed by processing system 116. If the generated signal for the particular detector 108 is the same as the known signal for the particular detector 108, processing system 112 may determine that an agent 102 is not present. If, however, the known signal for the particular detector 108 differs from the generated signal for the particular detector 108 (i.e., the generated signal constitutes an altered signal), processing system 116 may determine that an agent 102 is present (as the agent 102 absorbing a portion of the light emitted from the resonator 112 corresponding to the particular detector 108 may be the reason for the difference between the generated altered signal and the accessed signal).

Processing system 116 may be further operable to identify, in response to determining that an agent 102 is present, the agent 102 (or a family of the agent 102) based on the amount of light absorbed by the agent 102. For example, processing system 116 may determine an amount of light absorbed by the agent 102 by comparing the generated altered signal accessed from detectors 108 with the known signal associated with detectors 108. Having determined an amount of light absorbed by the agent 102 absorbed by each resonator 112, processing system 110 may access a plurality of agent profiles associated with a plurality of known agents 102 (e.g., from memory module 120 or any other suitable location in system 100), each profile indicating the light absorption characteristics of a particular known agent 102. For each resonator 112, processing system 116 may compare the determined amount of light absorbed by the agent 102 absorbed on the resonator 112 with the accessed agent profiles to determine the agent profile substantially matching the determined amount of light absorbed, thereby identifying the agent 102 absorbed on the surface of the resonator 112.

Furthermore, because different agents 102 may absorb different amounts of light at different peak wavelengths, the light absorption characteristics of the known agents 102 (as indicated in the agent profiles of the known agents 102) may account for the peak wavelengths at which absorption occurs. Additionally, because different resonators 112 of system 100 may be configured to transmit light at different peak wavelengths or ranges of peak wavelengths (as described above), the altered signals generated by detectors 108 and accessed by processing system 116 may be indicative of the peak wavelengths at which absorption occurs in the agent 102 absorbed on the surfaces of the corresponding resonators 112. Thus, in identifying the agent 102 absorbed on the surfaces of resonators 112 by matching the agent 102 with an agent profile, processing system 112 may account for the wavelengths at which absorption occurs, thereby increasing the accuracy of the identification.

As an additional example, each of the one or more resonators 112 may each be functionalized to attract a different agent 102 or family of agents 12 (as described above). Thus, by determining those detectors 108 generating altered signals (i.e., those detectors 108 generating signals that differ from the known signal, indicating absorption of light) and determining which agent 102 or family of agents 102 that the resonators 112 corresponding to those detectors 108 are functionalized to attract, processing system 116 may determine the agent 102 (or the family of the agent 102) absorbed on the surface of resonators 112.

Additionally or alternatively, processing system 116 may be operable to determine if an agent 102 is present (i.e., absorbed on the surface of one or more resonators 112) by analyzing the signals accessed from detectors 108 to determine if one or more of the accessed signals indicate a change in peak wavelength of light received by the detectors 108 (in a substantially similar manner to that discussed above with regard to changes intensity). For example, processing system 116 may access signals generated by detectors 108 and compare the signals accessed from detectors 108 with known signals associated with the detectors 108. If processing system 116 determines that any of the signals accessed from detectors 108 differ from known signals associated with detectors 108 (due to a change in peak wavelength of light received by detectors 108 caused by agent 102 absorbed by corresponding resonators 112), processing system 116 may determine that an agent 102 is present.

However, because the bandpass associated with a detector 108 (i.e., the range of peak wavelengths of light detectable to the detector 108) may be broader than the shift in wavelength caused by an agent 102 absorbed by a corresponding resonator 112, the detector 108 may not be able to detect a shift in wavelength caused by the agent 102. In other words, the signal generated by the detector 108 may be the same regardless of the peak wavelength shift caused by the agent 102. As a result, detectors 108 may have corresponding tunable filters 118, which may permit the detectors 108 to detect minute shift in wavelength that may be otherwise undetectable (as described in further detail below with regard to FIGS. 2A-2B).

Although a particular implementation of system 100 is illustrated and primarily described, the present disclosure contemplates any suitable implementation of system 100 according to particular needs. Furthermore, although a particular number of components of system 100 have been illustrated and primarily described above, the present disclosure contemplates system 100 including any suitable number of such components.

Figure 2A:
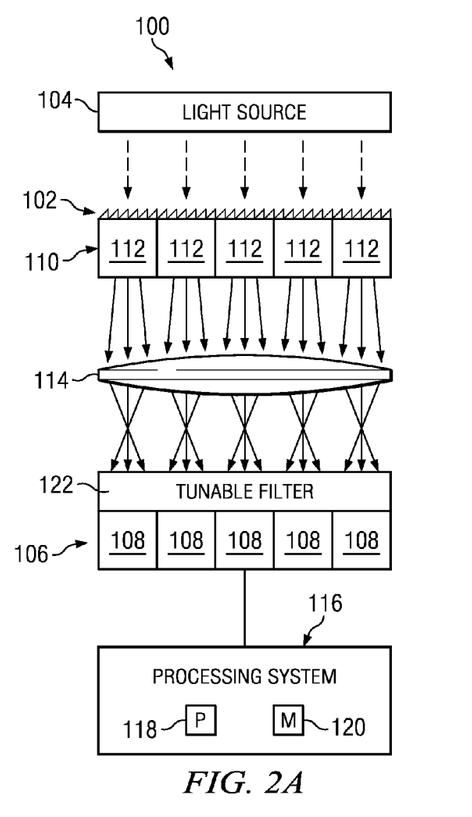
FIGS. 2A-2B illustrate an example alternative system for detecting an agent, according to certain embodiments of the present disclosure.
Figure 2B:
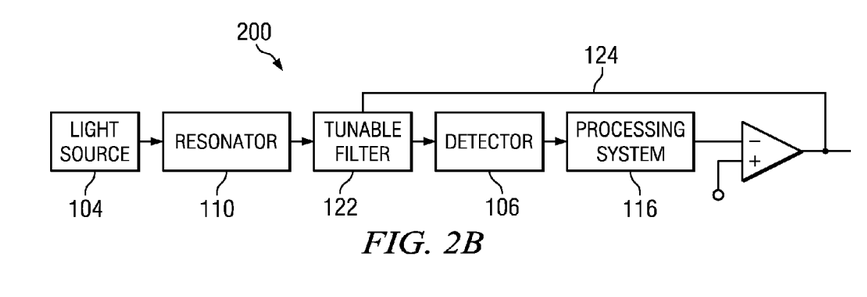

FIGS. 2A-2B illustrate an example alternative system 200 for detecting an agent 102, according to certain embodiments of the present disclosure. System 200 may include one or more light sources 104, a detector array 106 comprising one or more detectors 108, a resonator device 110 comprising one or more resonators 112 configured to receive (e.g., absorb) an agent 102, one or more lenses 114, and a processing system 116 (each of which is described above with regard to system 100 illustrated in FIG. 1). Moreover, each of these components of system 200 may be configured and operate in a substantially similar manner as described above with regard to FIG. 1.

In addition to the components of system 100 described above with regard to FIG. 1, system 200 may further include one or more tunable filters 122 each positioned between corresponding resonators 112 and detectors 108 of detector array 106 (each tunable filter 122 may correspond to one or more resonators 112 and one or more detectors 108 of detector array 106). Tunable filters 122 may be deposited directly onto detectors 108 (e.g., in a substrate overlaying detector array 106), located in close proximity to detectors 108, or otherwise located between corresponding resonators 112 and detectors 108. Because the bandpass associated with a detector 108 (i.e., the range of wavelengths of light for which the detector 108 is operable to generate a signal) may be broader than the shift in wavelength caused by an agent 102 absorbed on the surface of a resonator 112 (as described above), the detector 106 may not be able to detect the shift in wavelength caused by the agent 102. In other words, the signal generated by the detector 108 may be the same regardless of the peak wavelength shift caused by the agent 102. Accordingly, tunable filters 122 may facilitate the determination of an amount of the shift in wavelength caused by an agent 102 absorbed on the surface of a resonator 110, which may allow processing system 112 to determine the presence of and/or identify the agent 102, as described in further detail below.

Each tunable filter 122 may be operable to receive transmitted light from a corresponding resonator 112 and filter the transmitted light having peak wavelengths outside a range of peak wavelengths associated with (i.e., allowed to pass through) the tunable filter 122. The range of peak wavelengths associated with a tunable filter 122 (i.e., the bandpass of the tunable filter 122) may be narrower than the bandpass of the corresponding detector 108 such that transmitted light having wavelengths detectable by the detector 108 may be filtered by the tunable filter 122.

Furthermore, the range of peak wavelengths associated with (i.e., allowed to pass through) each tunable filter 122 may be variable. For example, a particular tunable filters 122 may have an associated first range of peak wavelengths such that the tunable filter 122 filters transmitted light received from the corresponding resonator 110 having wavelength outside the first range. Additionally, the particular tunable filter 122 may be operable to receive a signal. For example, the signal may be a voltage, a current, a digital signal, or any other suitable signal applied via a feedback control loop 124 controlled by processing system 116, as illustrated in FIG. 2B and described below. The received signal may cause the particular tunable filter 122 to filter transmitted light received from the corresponding resonator 112 having a wavelength outside a second range. In other words, the range of wavelengths outside which a tunable filter 122 filters transmitted light received from the corresponding resonator 112 may be dependent on an amount of signal (e.g., voltage) applied to the tunable filter 122.

Tunable filters 122 may be used (e.g., by processing system 116) in determining whether an agent 102 is present. As discussed above, each detector 108 of detector array 106 may be operable to generate a signal in response to light incident upon the detector 108 (i.e., light transmitted by the resonator 110 corresponding to the detector 108). However, because tunable filters 122 filter light transmitted by corresponding resonators 112, the corresponding detectors 108 may only generate a signal corresponding to light having a wavelength within the range of peak wavelengths associated with the corresponding tunable filter 122. In other words, transmitted light having peak wavelengths outside the range of peak wavelengths associated with the tunable filter 122 may not be received by the detector 106). Because an agent 102 absorbed on the surface of a resonator 122 may alter the peak wavelength at which the resonator 112 transmits light, the presence or absence of a signal generated by a detector 108 may be indicative of whether an agent 102 is present.

For example, a particular resonator 112 may have optical properties that cause the resonator 112 to transmit light having a known peak wavelength (in the absence of the agent 102) that falls within the range of peak wavelengths associated with the corresponding tunable filter 122. As a result, in the absence of an agent 102, a known signal will be generated by the corresponding detector 108 of detector array 106. However, an agent 102 absorbed on the surface of a resonator 110 may cause the light transmitted by the resonator 112 to have an altered peak wavelength that falls outside the range of peak wavelengths associated with the corresponding tunable filter 122. As a result, in the presence of the agent 102, a signal will not be generated by the corresponding detector 108 of detector array 106 (i.e., the transmitted light having the altered peak wavelength will not reach the detector 108 because the tunable filter 122 "blocks" the transmitted light).

Thus, if processing system 116 accesses the signals generated by the detectors 108 of detector array 106 (as described above) and determines that one or more of accessed signals differ from the known signals corresponding to those detectors 106 (because the one or more detectors 108 are not generating a signal since tunable filters 122 corresponding to the one or more detectors 108 are filtering the light transmitted by the corresponding resonators 112), processing system 116 may determine that an agent 102 has been absorbed on the surface of the one or more resonators 112.

Furthermore, if an agent 102 is determined to be present (e.g., based on the lack of a signal being generated by one or more detectors 108, as described above), tunable filters 122 may be used (e.g., by processing system 116) in identifying the agent 102. More particularly, tunable filters 122 may facilitate determining an amount of wavelength shift caused by an agent 102 absorbed on the surface of a resonator 110, and the amount of wavelength shift may be compared by processing system 112 with a number of known wavelength shifts associated with a number of known agents 102 to determine a match (i.e., the known wavelength shift having a value closest to the determined amount of wavelength shift). Based on the match, processing system 116 may identify the agent 102 absorbed on the surface of the resonator 112.

For example, as described above, the range of peak wavelengths associated with the tunable filters 122 may be variable based on an amount of signal (e.g., voltage) applied to the tunable filter 122. In other words, the amount of shift in the range of peak wavelengths associated with the tunable filters 122 may correspond to an amount of signal (e.g., voltage) applied to the tunable filter 122. Furthermore, processing system 116 (or any other suitable component of system 200) may be operable to maximize the signal being generated by detectors 108 of detector array 106 (i.e., maximize the intensity of light received by detectors 108) by controlling the amount of signal (e.g., voltage) applied to tunable filters 122 via a feedback control loop 124. Thus, based on the amount of signal (e.g., voltage) required to maximize the signal generated by a detector 108, processing system 116 may determine the wavelength shift in light transmitted by the corresponding resonator 112 between the known peak wavelength (i.e., when no agent 102 is absorbed on the corresponding resonator 112) and the altered peak wavelength (i.e., when no agent 102 is absorbed on the corresponding resonator 112).

Figure 3A:
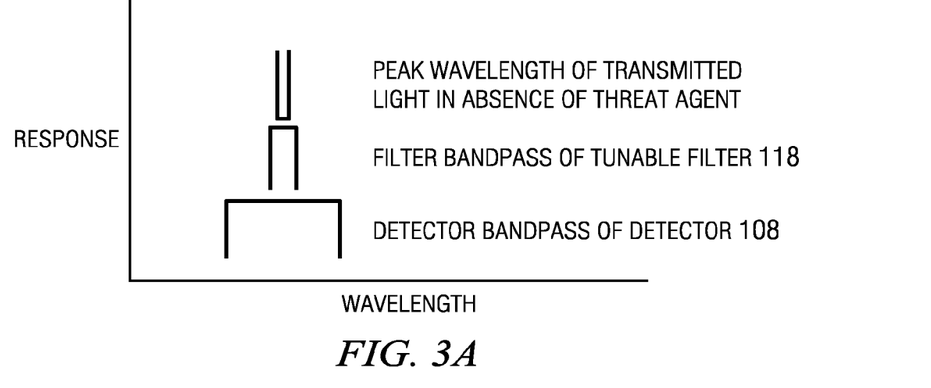
FIGS. 3A-3C illustrate example plots of response versus wavelength illustrating the operation of a tunable filter of the alternative system for detecting an agent illustrated in FIG. 2A-2B, according to certain embodiments of the present disclosure.
Figure 3B:
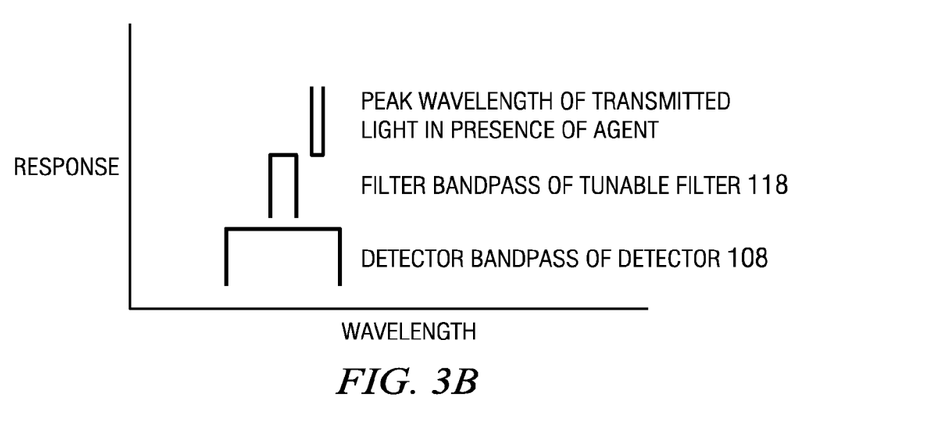
Figure 3C:
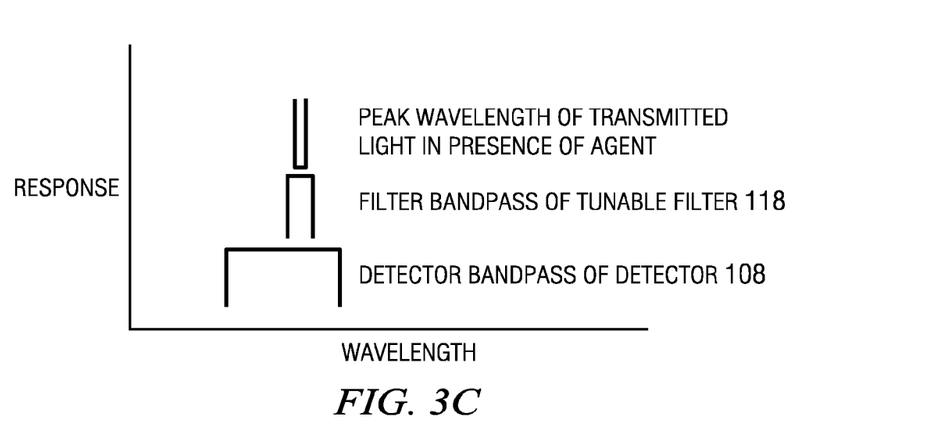

FIGS. 3A-3C illustrate example plots of response versus wavelength illustrating the operation of tunable filter 122 of system 200 (described above), according to certain embodiments of the present disclosure. FIG. 3A illustrates an example state of system 200 in which light is transmitted by a resonator 112 in the absence of an agent 102, the light having a known peak wavelength based on the optical properties of resonator 112. Furthermore, the known peak wavelength falls within the range of peak wavelengths associated with the corresponding tunable filter 122. Consequently, transmitted light having the known peak wavelength is not filtered by tunable filter 122 and reaches the corresponding detector 108 of detector array 106. Because the known peak wavelength falls within the range of wavelengths detectable by the corresponding detector 106 (i.e., within the bandpass of the corresponding detector 108), the corresponding detector 108 generates a signal (i.e., the known signal) corresponding to the received light.

FIG. 3B illustrates an example state of system 200 in which light is transmitted by a resonator 112 in the presence of an agent 102, the agent 102 changing the index of refraction of light received by resonator 112 such that the transmitted light has an altered peak wavelength. Furthermore, the altered peak wavelength falls outside the range of peak wavelengths associated with the corresponding tunable filter 122. Consequently, the transmitted light having the altered peak wavelength is filtered by tunable filter 122 and does not reach the corresponding detector 108 of detector array 106. Because the transmitted light does not reach the corresponding detector 106, the corresponding detector 106 does not generate a signal (which, as discussed above, indicates the presence of the agent 102).

FIG. 3C illustrates an example state of system 200 similar to that described above with regard to FIG. 3B except that in FIG. 3C a voltage has been applied to the corresponding tunable filter 122 via a feedback control loop 124, the applied voltage altering the range of peak wavelengths associated with the corresponding tunable filter 122 such that the altered peak wavelength of the transmitted light falls within the altered range of peak wavelengths associated with the corresponding tunable filter 122. Consequently, the transmitted light having the altered peak wavelength is not filtered by tunable filter 122 and reaches the corresponding detector 108 of detector array 106. Because the altered peak wavelength falls within the range of wavelengths detectable by the corresponding detector 106 (i.e., is within the bandpass of the corresponding detector 108), the corresponding detector 108 generates a signal (i.e., the altered signal) corresponding to the received light. Moreover, because the amount of shift in the range of peak wavelengths of the corresponding tunable filter 122 corresponds to the amount of applied voltage, the amount of shift in wavelength caused by the agent 102 may be determined.

Returning to FIG. 2, assuming that an agent 102 is absorbed on the surface of resonators 112 of resonator device 110, processing system 166 may access the voltage applied via feedback control loops 124 to each tunable filter 122 that maximizes the signal generated by the corresponding detectors 108 (the voltage applied being known to processing system due to the fact that the voltage is applied via feedback control loop 124). Based on the applied voltages, processing system 116 may determine the amount of wavelength shift in light transmitted by each resonator 112 caused by the agent 102 absorbed on each resonator 112. Processing system 116 may then compare the determined wavelength shifts with accessed known wavelength associated with a plurality of known agents 102 (e.g., from memory module 120) to determine a match for each resonator 112 (i.e., the known wavelength shift having a value closest to the determined amount of wavelength shift in light transmitted by each resonator 112). Based on the match, processing system 116 may identify the agent 102 absorbed on the surface of the resonator 112.

Furthermore, because different agents 102 may shift peak wavelengths to a greater degree at or near particular wavelengths, the known wavelengths shifts associated with the plurality of known agents profiles of agents 102 may take into account the wavelengths at which the peak wavelength shift occurs. Additionally, because different resonators 112 of system 100 may be configured to transmit light at different peak wavelengths or ranges of peak wavelengths (as described above), the voltages applied to the different tunable filters 122 accessed by processing system 116 may be indicative of an amount of wavelength shift associated with light having particular peak wavelengths (i.e., the known peak wavelengths of light transmitted by the resonators 112). Thus, in identifying the agent 102 absorbed on the surface of resonators 112 by matching the agent 102 with an agent profile, processing system 116 may account for the wavelengths at which different wavelength shifts occur, thereby increasing the accuracy of the identification.

In addition to determining the shift in peak wavelength of the transmitted light caused by an agent 102, processing system 116 may be further operable to determine an amount of light absorbed by the agent 102. For example, if an agent 102 is absorbed on the surface of a resonator 112 (causing a shift in peak wavelength of light transmitted by the resonator 110) and a voltage has been applied to the corresponding tunable filter 122 such that the transmitted light is received by the corresponding detector 108, it may be possible to determine an amount of light absorbed by the agent 102 based on the altered signal generated by the detector 108 in a manner substantially similar to that described above with regard to FIG. 1. Accordingly, processing system 116 may compare a determined shift in peak wavelength of transmitted light and the determined amount of transmitted light absorbed with corresponding components of a plurality of agent profiles to identify the agent 102. Because the identification is based on multiple characteristics of light (i.e., peak wavelength shift and absorption), the accuracy of the identification may be further increased.

FIG. 4 illustrates an example alternative system 400 for detecting an agent 102, according to certain embodiments of the present disclosure. System 400 may include a detector array 106 comprising one or more detectors 108, one or more lenses 114, and a processing system 116 (each of which is described above with regard to system 100 illustrated in FIG. 1). Moreover, each of these components of system 400 may be configured and operate in a substantially similar manner as described above with regard to FIG. 1.

Additionally, in system 400 light source 104 may comprise a plurality of emitter optical resonator 402, each emitter optical resonator 402 being optically coupled (e.g., via a waveguide 408) to a resonator 112 of resonator device 110. Furthermore, in system 400 each resonator 112 of resonator device 110 may comprise a functionalized optical resonator 406 optically coupled (e.g., via a waveguide 410) to a reference optical resonator 408. Although system 400 is depicted and primarily described as including a single emitter optical resonator 402 optically coupled to a single functionalized optical resonator 406/reference optical resonator 408 combination for purposes of simplicity, the present disclosure contemplates any suitable number emitter optical resonators 402 optically coupled to functionalized optical resonator 406/reference optical resonator 408 combinations.

Each of emitter optical resonator 402, functionalized optical resonator 404, and reference optical resonator 406, may include any device, system, or apparatus configured to form a standing wave of one or more wavelengths of visible and/or non-visible light. In certain embodiments, emitter optical resonator 402, functionalized optical resonator 404, and reference optical resonator 406 may each be configured to form a standing wave of the same peak wavelength(s).

For example, one or more of emitter optical resonator 402, functionalized optical resonator 404, and reference optical resonator 406 may comprise a waveguide configured in a closed loop known as an optical ring such that when light of the appropriate wavelength(s) is/are coupled to the loop, the light increases in intensity over multiple round-trips due to constructive interference. Other wavelengths of light may decrease in intensity due to destructive interference. Such optical rings may be made of materials, and may have sizes and configurations suitable to form standing waves of desired wavelength(s). As another example, one or more of emitter optical resonator 402, functionalized optical resonator 404, and reference optical resonator 406 may comprise an arrangement of mirrors known as an optical cavity and configured to form a standing wave for one or more wavelengths. Such optical cavities may be made of materials, and may have sizes and configurations suitable to form standing waves of desired wavelengths.

Emitter optical resonator 402 may include or be optically coupled to one more components configured to produce light at the peak wavelength(s) of emitter optical resonator 402. For example, emitter optical resonator 402 may include quantum dots and/or may be optically coupled to quantum dots (i.e., a semiconductor that may give off light based on the size of the quantum dot and the material from which it is made because of what is known as the quantum confinement effect).

Thus, emitter optical resonator 402 may function as a source of light which emits light at the peak wavelength or a plurality of peak wavelengths (e.g. a group of wavelengths or a continuous band of wavelengths).

In embodiments in which emitter optical resonator 402 includes quantum dots, quantum dots may be added to emitter optical resonator 402 using any suitable technique. For example, in embodiments where emitter optical resonator 202 comprises an optical ring, quantum dots may be formed within or adjacent to the optical ring using known semiconductor manufacturing techniques. As another example, in embodiments where emitter optical resonator 202 comprises an optical cavity, portions of the optical cavity may be coated with quantum dots created by colloidal synthesis.

Emitter optical resonator 202 may be optically coupled to functionalized optical resonator 404 via waveguide 408. Waveguide 408 may include any system, device, or apparatus to transmit light between emitter optical resonator 402 and functionalized optical resonator 404. In certain embodiments, waveguide 408 may comprise a dielectric waveguide, a structure in which a dielectric material with high permittivity, and thus high index of refraction (e.g., glass), is surrounded by a material with lower permittivity (e.g., air), permitting the waveguide to guide optical waves via total internal reflection.

In certain embodiments, functionalized optical resonator 404 may have approximately the same peak wavelength(s) as emitter optical resonator 402. Additionally, functionalized optical resonator 404 may configured such that an agent 102 may be received on a surface of functionalized optical resonator 404. For example, functionalized optical resonator 206 may be functionalized (e.g., by coating a surface with artificial antibodies using a polymer technique) such that functionalized optical resonator 206 attracts only certain agents 102 or families of agents 102.

Furthermore, an agent 102 being absorbed by functionalized optical resonator 404 may change one or more characteristics of light transmitted by functionalized optical resonator 404. For example, in embodiments where functionalized optical resonator 404 comprises an optical ring, an agent 102 being absorbed by functionalized optical resonator 404 may alter its refractive index, which it turn may alter the peak wavelength(s) of light transmitted by functionalized optical resonator 404. As another example, in embodiments where functionalized optical resonator 404 comprises an optical cavity, an agent 102 being absorbed by functionalized optical resonator 404 may reduce the intensity of light transmitted by the optical cavity.

Functionalized optical resonator 404 may be coupled to reference optical resonator 406 via waveguide 410. Waveguide 410 may include any system, device, or apparatus to transmit light between functionalized optical resonator 404 and reference optical resonator 406. In certain embodiments, waveguide 410 may comprise a dielectric waveguide. In the same or alternative embodiments, waveguide 410 may be identical or similar to waveguide 408.

In certain embodiments, reference optical resonator 406 may have approximately the same peak wavelength(s) as emitter optical resonator 402 and functionalized optical resonator 404. Reference optical resonator 406 may be positioned relative to lens 114 such that light transmitted by reference optical resonator 406 is focused onto one or more corresponding detectors 108 of detector array 106, the one or more corresponding detectors 108 being operable to generate a signal corresponding to the transmitted light (as discussed above with regard to FIG. 1). Processing system 116 may then access signals generated by the one or more corresponding detectors 108 of detector array 106 and determine if an agent 102 is present (i.e., absorbed by functionalized optical resonator 404).

In certain embodiments, processing system 116 determines if an agent 102 is present by analyzing the accessed signals to determine if one or more of the signals indicate a change in intensity of light received by the detectors 108 generating the one or more signals. Because an agent 102 absorbed by functionalized optical resonator 404 may shift the peak wavelength(s) of light transmitted by functionalized optical resonator 404 and such a shift may cause a mismatch between the peak wavelength(s) of functionalized optical resonator 404 and the wavelength(s) of light emitted by emitter optical resonator 402, functionalized optical resonator 404 may filter all or a portion of the light received from emitter optical resonator 402. As a result, the intensity of light transmitted from functionalized optical resonator 404 to reference optical resonator 406 (and subsequently received by the one or more corresponding detectors of detector array 106) may be less than that received from emitter optical resonator 402. Additionally or alternatively, the agent 102 itself may absorb some of the light emitted by emitter optical resonator 404, thereby decreasing the intensity of light passing through functionalized optical resonator 404.

By accessing signals generated by detectors 108 of detector array 106 and comparing those accessed signal to known signals (i.e., signals generated by detectors 108 in the absence of an agent 102), processing system 116 may determine if an agent 102 is absorbed by functionalized optical resonator 404 (in a substantially similar manner to that described above with regard to FIG. 1). Additionally, if an agent 102 is present, processing system may be further operable to identify the agent 102. For example, processing system may determine based on the accessed, an amount of intensity loss and compare that determined amount to absorption characteristics of known agents 102 (in a substantially similar manner to that described above with regard to FIG. 1)

Figure 5:
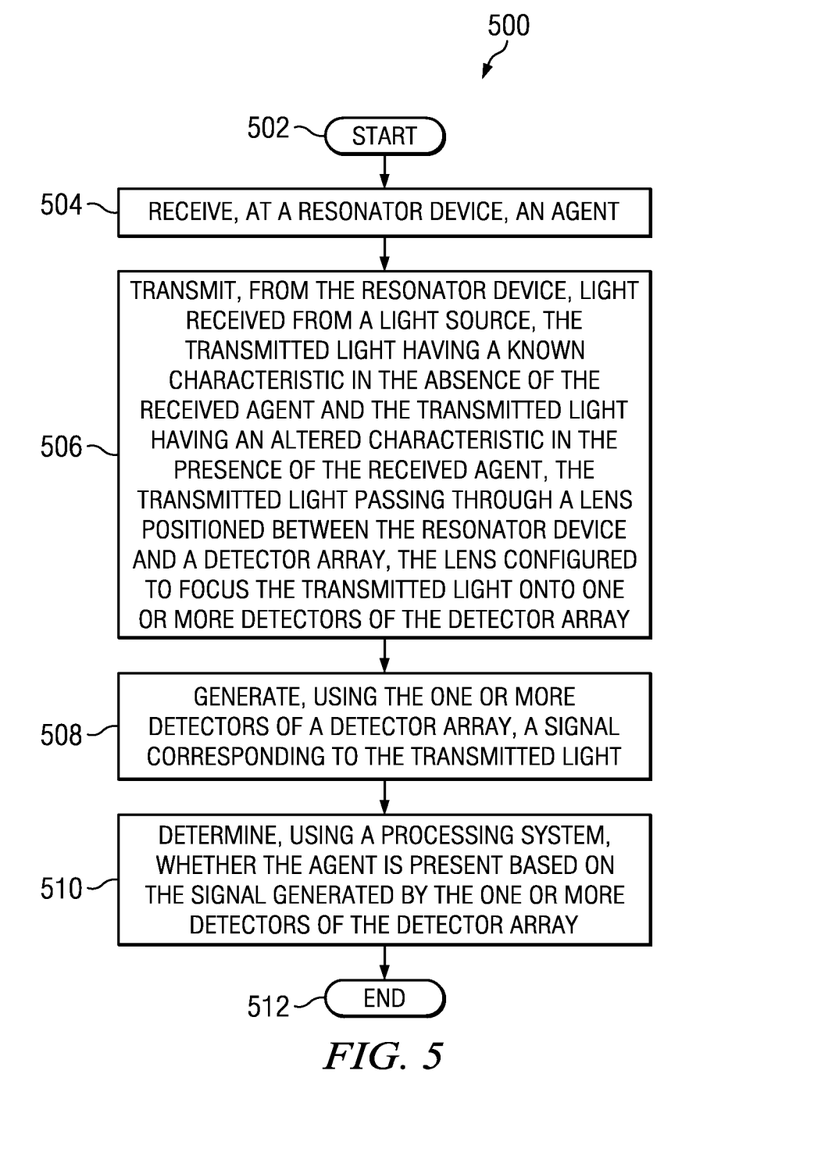
FIG. 5 illustrate an example method for detecting an agent, according to certain embodiments of the present disclosure.

FIG. 5 illustrate an example method 500 for detecting an agent 102, according to certain embodiments of the present disclosure. Although for purposes of method 500 is described in the context of a single resonator 112 of resonator device 110, the present disclosure contemplates that the method is applicable to any suitable number of resonators 112 of resonator device 110.

The method begins at step 502. At step 504, resonator 112 of resonator device 110 receives an agent 102. As discussed above with regard to FIG. 1, resonators 112 of resonator device 110 may be functionalized to receive different agents 102 or families of agent. Accordingly, depending on the agent 102, particular ones of resonators 112 of resonator device 110 may receive agent 102.

At step 504 the resonator 112 receiving the agent 102 transmits light received from a light source to a corresponding detector 108 of detector array 106. The transmitted light passes through a lens 114 positioned between the resonator device 110 and detector array 106, lens 114 configured to focus the transmitted light onto the corresponding detector 108 of detector array 106. The light transmitted to the corresponding detector 108 of detector array 106 has a known characteristic in the absence of the received agent (e.g., based on the optical properties of resonator 112) and an altered characteristic in the presence of the received agent.

For example, a received agent 102 may absorb a portion of the light received by the resonator 112 such that the light transmitted by the resonator 112 has an altered intensity in the presence of agent 102 that is less than a known intensity in the absence of agent 102 (as described above with regard to FIG.

1). Additionally or alternatively, a received agent 102 may change the index of refraction the light received by the resonator 112 (i.e., change the peak wavelength of the light) such that the light transmitted by the resonator 112 has an altered peak wavelength in the presence of agent 102 that is different than a known peak wavelength in the absence of agent 102 (as described above with regard to FIG. 1)

At step 506, the corresponding detector 108 of detector array 106 generates a signal corresponding to the light transmitted by the resonator 112. For example, detector 108 of detector array 106 may generate a known signal when the transmitted light has a known characteristic (e.g., intensity and/or peak wavelength) and an altered signal when the he transmitted light has a known characteristic (e.g., intensity and/or peak wavelength).

At step 508, processing system 116 determines whether the agent 102 is present based on the signal generated by the corresponding detector 108 of the detector array 106. For example, processing system 116 may determine that the generated signal differs from a known signal (i.e., processing system 116 may determine that the generated signal is an altered signal), the altered signal indicating the presence of agent 102. Additionally or alternatively, processing system 116 may determine that the absence of a generated signal indicates the presence of an agent (e.g., in embodiments in which a tunable filter is positioned between detector 108 and lens 114, as described above with regard to FIGS. 2A-3C). The method ends at step 510.

Although the present invention has been described with several embodiments, diverse changes, substitutions, variations, alterations, and modifications may be suggested to one skilled in the art, and it is intended that the invention encompass all such changes, substitutions, variations, alterations, and modifications as fall within the spirit and scope of the appended claims.

What is claimed is:

1. An agent detection system, comprising:
a resonator device configured to:
   receive an agent;
   transmit light received from a light source, the transmitted light having a known intensity in the absence of the received agent and the transmitted light having an altered intensity in the presence of the received agent, the altered intensity being less than the known intensity;
a lens positioned between the resonator device and a detector array, the lens configured to focus the transmitted light onto one or more detectors of the detector array, the one or more detectors of the detector array operable to generate a signal corresponding to the transmitted light, the signal generated by the one or more detectors of the detector array comprising:
   a known signal when the transmitted light has the known intensity; and
   an altered signal when the transmitted light has the altered intensity; and
a processing system operable to:
   determine whether the agent is present based on the signal generated by the one or more detectors of the detector array by:
      accessing the altered signal generated by the detector array; and
      determining that the altered signal differs from the known signal; and
   identify the agent as one of a number of known agents by:
      determining an amount of light absorbed by the agent by comparing the altered signal with the known signal; and
      comparing the determined amount of light absorbed with absorption characteristics of the number of known agents.

2. The system of claim 1, wherein the detector array comprises a focal plane array (FPA).

3. The system of claim 1, wherein:
the resonator device is maintained at a first temperature; and
the detector array is maintained at a second temperature, the second temperature being different than the first temperature.

4. The system of claim 1, wherein:
the light source comprises an emitter optical resonator configured to emit the light received by the resonator device, the emitter optical resonator being optically coupled to the resonator device via a first waveguide; and
the resonator device comprises:
   a functionalized optical resonator configured to:
      receive the light emitted by the emitter optical resonator via the first waveguide; and
      receive the agent; and
   a reference optical resonator optically coupled to the functionalized optical resonator via a second waveguide, the reference optical resonator configured to transmit the light received from the functionalized optical resonator via the second waveguide, the transmitted light having the known intensity in the absence of the agent on the functionalized optical resonator and the transmitted light having the altered intensity in the presence of the agent on the functionalized optical resonator.

5. The system of claim 4, wherein the emitter optical resonator, the functionalized optical resonator, and the reference optical resonator are each formed on a substrate.

6. The system of claim 4, wherein at least one of the emitter optical resonator, the functionalized optical resonator, and the reference optical resonator comprises a chalcogenide glass.

7. The system of claim 4, wherein at least one of the emitter optical resonator, the functionalized optical resonator, and the reference optical resonator comprises an optical ring.

8. The system of claim 4, wherein the emitter optical resonator comprises a plurality of quantum dots configured to emit light having a known intensity and a known peak wavelength.

9. A method for detecting an agent, comprising:
receiving, at a resonator device, an agent;
transmitting, from the resonator device, light received from a light source, the transmitted light having a known intensity in the absence of the received agent and the transmitted light having an altered intensity in the presence of the received agent, the altered intensity being less than the known intensity, the transmitted light passing through a lens positioned between the resonator device and a detector array, the lens configured to focus the transmitted light onto one or more detectors of the detector array;
generating, using the one or more detectors of a detector array, a known signal when the transmitted light has the known intensity and an altered signal when the transmitted light has the altered intensity;
determining, using a processing system, whether the agent is present based on the signal generated by the one or more detectors of the detector array including:

accessing the altered signal generated by the detector array; and determining that the altered signal differs from the known signal; and identifying the agent as one of a number of known agents by:

determining an amount of light absorbed by the agent by comparing the altered signal with the known signal; and comparing the determined amount of light absorbed with absorption characteristics of the number of known agents.

10. The system of claim 9, wherein the detector array comprises a focal plane array (FPA).

11. The method of claim 9, wherein:

the resonator device is maintained at a first temperature; and the detector array is maintained at a second temperature, the second temperature being different than the first temperature.

12. The method of claim 9, wherein:

the light source comprises an emitter optical resonator configured to emit the light received by the resonator device, the emitter optical resonator being optically coupled to the resonator device via a first waveguide; and the resonator device comprises:

a functionalized optical resonator configured to:
receive the light emitted by the emitter optical resonator via the first waveguide; and
receive the agent; and a reference optical resonator optically coupled to the functionalized optical resonator via a second waveguide, the reference optical resonator configured to transmit the light received from the functionalized optical resonator via the second waveguide, the transmitted light having a the known intensity in the absence of the agent on the functionalized optical resonator and the transmitted light having the altered intensity in the presence of the agent on the functionalized optical resonator.

13. The method of claim 12, wherein the emitter optical resonator, the functionalized optical resonator, and the reference optical resonator are each formed on a substrate.

14. The method of claim 12, wherein at least one of the emitter optical resonator, the functionalized optical resonator, and the reference optical resonator comprises a chalcogenide glass.

15. The method of claim 12, wherein at least one of the emitter optical resonator, the functionalized optical resonator, and the reference optical resonator comprises an optical ring.

16. The method of claim 12, wherein the emitter optical resonator comprises a plurality of quantum dots configured to emit light having the known intensity and a known peak wavelength.

17. A method for detecting an agent, comprising:

receiving, at a resonator device, an agent;

transmitting, from the resonator device, light received from a light source, the transmitted light having a known peak wavelength in the absence of the received agent and the transmitted light having an altered peak wavelength in the presence of the received agent, the altered peak wavelength being different than the known peak wavelength, the transmitted light passing through a lens positioned between the resonator device and a detector array, the lens configured to focus the transmitted light onto one or more detectors of the detector array;

generating, using the one or more detectors of a detector array, a signal corresponding to the transmitted light;

filtering, using a filter device positioned between the lens and the one or more detectors of the detector array, the transmitted light having the altered peak wavelength such that the transmitted light having the altered peak wavelength does not reach the one or more detectors of the detector array, the filter device configured to receive the transmitted light from the resonator device and filter the transmitted light having a peak wavelength outside a first range of peak wavelengths, the known peak wavelength being within the first range and the altered peak wavelength being outside the first range; and determining, using a processing system, whether the agent is present based on the signal generated by the one or more detectors of the detector array, including determining that the one or more detectors of the detector array are not generating a signal, the absence of a signal being generated by the one or more detectors of the detector array indicating the presence of the agent.

18. The method of claim 17, further comprising:

receiving, at the filter device, a feedback signal in response to the determination that the one or more detectors of the detector array are not generating a signal, the received feedback signal causing the filter device to filter transmitted light having a peak wavelength outside a second range of peak wavelengths, the altered peak wavelength being within the second range of peak wavelengths; and identifying, using the processing system, the agent as one of a number of known agents by:

accessing an amount of the feedback signal received by the filter device;

determining, based on the amount of the feedback signal applied to the filter device, a wavelength shift corresponding to the difference between the known peak wavelength and the altered peak wavelength; and comparing the determined wavelength shift with a number of wavelength shifts corresponding to the number of known agents.

19. An agent detection system, comprising:

an emitter optical resonator comprises a plurality of quantum dots, the emitter optical resonator configured to emit light having a known intensity and a known peak wavelength;

a functionalized optical resonator comprising an optical ring, the functionalized optical resonator configured to:
receive an agent; and
receive the light emitted by the emitter optical resonator from the emitter optical resonator via a first waveguide;

a reference optical resonator comprising an optical ring, the reference optical resonator configured to:
receive the light emitted by the emitter optical resonator from functionalized optical resonator via a second waveguide; and
transmit the light received from the functionalized optical resonator, the transmitted light having a known characteristic in the absence of the agent on the functionalized optical resonator and the transmitted light having an altered characteristic in the presence of the agent on the functionalized optical resonator;

a lens positioned between the reference optical resonator and a detector array, the lens configured to focus the light transmitted by the reference optical resonator onto one or more detectors of the detector array, the one or more detectors of the detector array operable to generate a signal corresponding to the transmitted light; and a processing system operable to determine whether the agent is present based on the signal generated by the one or more detectors of the detector array.

20. The system of claim 19, wherein:
the known characteristic comprises the known peak wavelength; and
the altered characteristic comprises an altered peak wavelength, the altered peak wavelength being different than the known peak wavelength.

21. The system, of claim 20, further comprising:
a filter device positioned between the lens and the one or more detectors of the detector array, the filter device configured to receive transmitted light from the resonator device and filter transmitted light having a peak wavelength outside a first range of peak wavelengths, the known peak wavelength being within the first range and the altered peak wavelength being outside the first range;
the processing system operable to determine whether the agent is present by determining that the one or more detectors of the detector array are not generating a signal, the absence of a signal being generated by the one or more detectors of the detector array indicating the presence of the agent.

22. The system of claim 21, wherein:
the filter device is operable to receive a feedback signal in response to the determination that the one or more detectors of the detector array are not generating a signal, the received feedback signal causing the filter device to filter transmitted light having a peak wavelength outside a second range of peak wavelengths, the altered peak wavelength being within the second range of peak wavelengths; and
the processing system is further operable to identify the agent as one of a number of known agents by:
accessing an amount of the feedback signal received by the filter device;
determining, based on the amount of the feedback signal applied to the filter device, a wavelength shift corresponding to the difference between the known peak wavelength and the altered peak wavelength; and
comparing the determined wavelength shift with a number of wavelength shifts corresponding to the number of known agents.

23. The system of claim 19, wherein the emitter optical resonator, the functionalized optical resonator, and the reference optical resonator are each formed on a substrate.

24. The system of claim 19, wherein at least one of the emitter optical resonator, the functionalized optical resonator, and the reference optical resonator comprises a chalcogenide glass.

* * * * *